United States Patent
Mahdavinia et al.

(10) Patent No.: US 12,310,994 B2
(45) Date of Patent: May 27, 2025

(54) COMPOSITIONS AND METHODS OF TREATMENT FOR CHRONIC RHINOSINUSITIS

(71) Applicant: Rush University Medical Center, Chicago, IL (US)

(72) Inventors: Mahboobeh Mahdavinia, Chicago, IL (US); Sukhpreet Batra, River Forest, IL (US)

(73) Assignee: Rush University Medical Center, Chicago, IL (US)

( * ) Notice: Subject to any disclaimer, the term of this patent is extended or adjusted under 35 U.S.C. 154(b) by 907 days.

(21) Appl. No.: 16/973,243

(22) PCT Filed: Jun. 12, 2019

(86) PCT No.: PCT/US2019/036700
§ 371 (c)(1),
(2) Date: Dec. 8, 2020

(87) PCT Pub. No.: WO2019/241339
PCT Pub. Date: Dec. 19, 2019

(65) Prior Publication Data
US 2021/0236561 A1     Aug. 5, 2021

Related U.S. Application Data

(60) Provisional application No. 62/684,019, filed on Jun. 12, 2018.

(51) Int. Cl.
*A61K 35/74*     (2015.01)
*A61K 45/06*     (2006.01)

(52) U.S. Cl.
CPC .............. *A61K 35/74* (2013.01); *A61K 45/06* (2013.01)

(58) Field of Classification Search
CPC ...... A61K 35/74; A61K 45/06; A61K 9/0043; A61P 11/02; A61P 11/06
See application file for complete search history.

(56) References Cited

U.S. PATENT DOCUMENTS

| | | |
|---|---|---|
| 2015/0097039 A1 | 4/2015 | Narendra et al. |
| 2017/0143621 A1 | 5/2017 | Baum et al. |

FOREIGN PATENT DOCUMENTS

| | | |
|---|---|---|
| WO | 2018073276 A1 | 4/2018 |

OTHER PUBLICATIONS

Bomar L et al. Corynebacterium accolens releases antipneumococcal free fatty acids from human nostril and skin surface triacylglycerols. 2016. mBio. 1-13. (Year: 2016).*

Nagalingam N et al. Probiotic strategies for treatment of respiratory diseases. 2013. Trends in Microbiology. 21, 9. 485-492. (Year: 2013).*

Dixon AE. Rhinosinusitis and asthma: the missing link. 2009. Current Opinion in Pulmonary Medicine. 15:19-24. (Year: 2009).*

Aanaes K. Bacterial sinusitis can be a focus for initial lung colonisa¬tion and chronic lung infection in patients with cystic fibrosis. J Cyst Fibros. 2013;12(5uppl 2):51-520.

Bachert, C., Zhang, N., van Zele, T., Gevaert, P., Patou, J., and van Cauwenberge, P. *Staphylococcus aureus* enterotoxins as immune stimulants in chronic rhinosinusitis. Clin Allergy Immunol. 2007; 20: 163-175.

Biesbroek, G., Tsivtsivadze, E., Sanders, E.A., Montijn, R., Veenhoven, R.H., Keijser, B.J. et al. Early respiratory microbiota composition determines bacterial succession patterns and respiratory health in children. Am J Respir Crit Care Med. 2014; 190: 1283-1292.

Caporaso, J.G., Lauber, C.L., Walters, W.A., Berg-Lyons, D., Huntley, J., Fierer, N. et al. Ultra-high-throughput microbial community analysis on the Illumina HiSeq and MiSeq platforms. Isme J. 2012;6: 1621-1624.

Cardenas PA, Cooper PJ, Cox MJ, et al. Upper airways microbiota in antibiotic-naive wheezing and healthy infants from the tropics of rural Ecuador. PLoS One. 2012;7(10):e46803.

Chang, K.R., Tay, A.S., Li, C., Ng, A.H., Wang, J., Suri, B.K. et al. Whole metagenome profiling reveals skin microbiome-dependent susceptibility to atopic dermatitis flare. Nat Microbiol. 2016; 1: 16106.

Clarke, K.R. Non-parametric multivariate analyses of changes in community structure. Aust J Ecol. 1993; 18: 117-143.

David J, Bell RE, Clark GC. Mechanisms of disease: host-pathogen interactions between *burkholderia* species and lung epithelial cells. Front Cell Infect Microbiol. 2015;5:80.

Dixon AE, Kaminsky DA, Holbrook JT, Wise RA, 5hade DM, Irvin CG. Allergic rhinitis and sinusitis in asthma: differential effects on symptoms and pulmonary function. Chest. 2006;130(2):429-435.

Fokkens WJ, Lund VJ, Mullol J, et al. EPOS 2012: European position paper on rhinosinusitis and nasal polyps 2012. A summary for otorhinolaryngologists. Rhinology. 2012;50(1):1-12.

Gihring, T.M., Green, S.J., and Schadt, C.W. Massively parallel rRNA gene sequencing exacerbates the potential for biased community diversity comparisons due to variable library sizes. Environ Microbiol. 2012; 14: 285-290.

Green, S.J., Venkatramanan, R., and Naqib, A. Deconstructing the polymerase chain reaction: understanding and correcting bias associated with primer degeneracies and primer-template mismatches. PLoS One. 2015; 10: e0128122.

Hilty, M., Burke, C., Pedro, H., Cardenas, P., Bush, A., Bossley, C. et al. Disordered microbial communities in asthmatic airways. PLoS One. 2010; 5: e8578.

(Continued)

*Primary Examiner* — Paul J Holland

(74) *Attorney, Agent, or Firm* — Barnes & Thornburg LLP

(57) ABSTRACT

Methods and compositions for treating sinusitis in a subject are provided. The methods include administering to the subject an effective amount of a composition that stimulates growth or activity of a genus of bacteria that is decreased relative to a control subject not having sinusitis and/or inhibiting growth or activity of a genus of bacteria that is increased relative to the control subject.

13 Claims, No Drawings

(56) References Cited

OTHER PUBLICATIONS

Huang Y J, Marsland BJ, Bunyavanich S, et al. The microbiome in allergic disease: current understanding and future opportunities—2017 PRACTALL document of the American academy of allergy, asthma & immunology and the European academy of allergy and clinical immunology. J Allergy Clin Immunol. 2017;139(4):1099-1110.

International Preliminary Report on Patentability, issued in PCT/US2019/036700, dated Dec. 15, 2020.

International Search Report, issued in PCT/US2019/036700, dated Oct. 18, 2019.

Keshavarzian, A., Green, S.J., Engen, P.A., Voigt, R.M., Naqib, A., Forsyth, C.B. et al. Colonic bacterial composition in Parkinson's disease. Mov Disord. 2015; 30: 1351-1360.

Lal, D., Keim, P., Delisle, J., Barker, B., Rank, M.A., Chia, N. et al. Mapping and comparing bacterial microbiota in the sinonasal cavity of healthy, allergic rhinitis, and chronic rhinosinusitis subjects. Int Forum Allergy Rhinol. 2017; 7: 561-569.

Langille, M.G., Zaneveld, J., Caporaso, J.G., McDonald, D., Knights, D., Reyes, J.A. et al. Predictive functional profiling of microbial communities using 16S rRNA marker gene sequences. Nat Biotechnol. 2013; 31: 814-821.

Lee TJ, Fu CH, Wang CH, et al. Impact of chronic rhinosinusitis on severe asthma patients. PLoS One. 2017;12(2): e0171047.

Lucas SK, Yang R, Dunitz JM, Boyer HC, Hunter RC. 16S rRNA gene sequencing reveals site-specific signatures of the upper and lower airways of cystic fibrosis patients. J Cyst Fibros. 2018;17(2):204-212.

Mahdavinia M, Engen PA, LoSavio PS, et al. The nasal microbiome in patients with chronic rhinosinusitis: Analyzing the effects of atopy and bacterial functional pathways in 111 patients. J Allergy Clin Immunol. 2018;142:287-290.

Mahdavinia, M., Keshavarzian, A., Tobin, M.C., Landay, A.L., and Schleimer, R.P. A comprehensive review of the hasal microbiome in chronic rhinosinusitis (CRS). Clin Exp Allergy. 2016; 46: 21-41.

Navarro J, Rainisio M, Harms HK, et al. Factors associated with poor pulmonary function: cross-sectional analysis of data from the ERCF. European Epidemiologic Registry of Cystic Fibrosis. Eur Respir J. 2001;18(2):298-305.

Ramakrishnan VR, Hauser LJ, Feazel LM, Ir D, Robertson CE, Frank DN. Sinus microbiota varies among chronic rhinosinusitis phenotypes and predicts surgical outcome. J Allergy Clin Immunol. 2015;136 (2):334-342. e1.

Stefka, A.T., Feehley, T., Tripathi, P., Qiu, J., McCoy, K., Mazmanian, S.K. et al. Commensal bacteria protect against food allergen sensitization. Proc Natl Acad Sci U S A. 2014; 111: 13145-13150.

Stephenson, M.F., Mfuna, L., Dowd, S.E., Wolcott, R.D., Barbeau, J., Poisson, M. et al. Molecular characterization of the polymicrobial flora in chronic rhinosinusitis. J Otolaryngol Head Neck Surg. 2010; 39: 182-187.

Teo SM, Mok D, Pham K, et al. The infant nasopharyngeal micro biome impacts severity of lower respiratory infection and risk of asthma development. Cell Host Microbe. 2015;17(5):704-715.

Zemanick, E.T., Wagner, B.D., Robertson, C.E., Stevens, M.J., Szefler, S.J., Accurso, F.J. et al.Assessment of airway microbiota and inflammation in cystic fibrosis using multiple sampling methods. Ann Am Thorac Soc. 2015; 12: 221-229.

\* cited by examiner

COMPOSITIONS AND METHODS OF TREATMENT FOR CHRONIC RHINOSINUSITIS

RELATED APPLICATIONS

The present patent application is a National Stage application of International Application No. PCT/US2019/036700, filed Jun. 12, 2019, which claims the benefit of the filing date of U.S. Provisional Patent Application No. 62/684,019, filed Jun. 12, 2018, the contents of both of which are hereby incorporated by reference.

TECHNICAL FIELD

The present disclosure is generally directed to compositions and methods for modifying the microbiome in the nasal cavity and more specifically directed to compositions and methods for modifying the microbiome in the nasal cavity of subjects having chronic sinusitis and/or asthma.

BACKGROUND

Chronic rhinosinusitis (CRS) is a chronic inflammatory disease involving the mucosal tissue of the upper airways, including the nose and paranasal sinuses. The inflammatory milieu in patients with CRS is thought to be affected by or even possibly initiated by commensal microbes, pathogens, and their products[1,2] Asthma is a related chronic inflammatory disease of the lower airways that is often comorbid with CRS. Uncontrolled upper airway inflammation in the context of CRS is associated with lower airway T-helper-2-mediated inflammation and recalcitrant asthma, however; the underlying mechanism of this link is rather complicated and currently under investigation. Rhinosinusitis is also linked to increased asthma severity and exacerbation rate. Nevertheless, fundamental questions regarding the mechanisms of chronic mucosal inflammation in CRS and how chronic sinonasal inflammation may affect the lower airways remain unanswered. Considering the likely possibility that microorganisms extant in the upper airways will be aspirated into the lungs, studies of the sinonasal microbiome in the context of lung health appear to be worthwhile. Microbiome studies provide important knowledge about both commensal and pathogenic microbes residing in the airways.[2]

To date, only a few studies have evaluated the nasal microbiome in patients with CRS. There has been a lack of consistency in these studies in terms of both abundance and the α-diversity indices of bacteria.2 Thus far, all previous studies have evaluated the microbiome in terms of its α-diversity (ie, richness) and relative abundance (RA) in each operational taxonomic unit (OTU) that alone do not provide any in-depth information on the potential functional effect of the nasal microbiota. The present disclosure evaluates sinonasal bacterial communities by using predictive functional profiling and identifies aspects of the microbiome for modulation to treat CRS and/or asthma.

SUMMARY

In some aspects, methods for treating sinusitis in a subject are provided. The methods include administering to the subject an effective amount of a composition that stimulates growth or activity of a genus of bacteria that is decreased relative to a control subject not having sinusitis and/or inhibiting growth or activity of a genus of bacteria that is increased relative to the control subject.

In other aspects, compositions for treating sinusitis in a subject are provided. Compositions include a bacterial composition including bacteria from the genus *Corynebacterium* and/or the genus *Peptoniphilus*

DETAILED DESCRIPTION

Definitions

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of assay methods, methods of analysis, or other aspects, are disclosed. It is to be understood that each such disclosed feature or features can be combined with the generalized features discussed, to form a disclosed embodiment of the present invention.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

As used herein, "microbiome" refers to the population of microorganisms that are present in a particular environment, such as the nasal cavity, the gut or digestive system, the urogenital tract, the mouth, the oral cavity, and the like. A microbiome is a microbial population defined by the diversity as well as the relative amounts of bacteria that compose a particular microbiome.

The term "therapeutic effect" as used herein means an effect which induces, ameliorates or otherwise causes an improvement in the pathological symptoms, disease progression or physiological conditions associated with a disorder, for example sinusitis, such as chronic rhinosinusitis or asthma, of a human or veterinary subject. The term "therapeutically effective amount" as used with respect to an agent means an amount of the agent which imparts a therapeutic effect to the human or veterinary subject.

Methods of Treatment

In some aspects, methods for treating sinusitis are provided. The methods include administering to the subject an effective amount of a composition that stimulates growth or activity of a genus of bacteria that is decreased relative to a control subject not having sinusitis and/or inhibiting growth or activity of a genus of bacteria that is increased relative to the control subject.

In some embodiments, the methods provided herein include administering a composition including bacteria to a subject. In some embodiments, the bacteria are from the genus *Corynebacterium* and/or the genus *Peptoniphilus*. In some embodiments, the bacteria from both the genus *Corynebacterium* and the genus *Peptoniphilus* are administered concurrently or sequentially. In some embodiments, an additional active agent is administered concurrently or sequentially with the bacteria. In embodiments, the additional active material is an antibiotic that is bacteriostatic or bactericidal to the genus *Streptoococcus* and/or the genus *Burkholderia*.

In embodiments, a composition is administered orally. In embodiments, a composition is administered nasally. In some embodiment the composition is administered with a pharmaceutically acceptable excipient. In some embodiments, the pharmaceutically acceptable excipient is suitable for nasal administration.

The exact dose and formulation will depend on the purpose of the treatment, and will be ascertainable by one skilled in the art using known techniques (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

Pharmaceutical Compositions

In some aspects, compositions are provided that include a bacterial composition. The bacterial composition may include bacteria from the genus *Corynebacterium* and/or the genus *Peptoniphilus*. In some embodiments, the bacteria composition includes the genus *Corynebacterium* and/or the genus *Peptoniphilus* that are obtained from the oral cavity, nasal cavity, or anterior nares of warm-blooded vertebrates (e.g., humans).

Such pharmaceutical compositions may take any physical form necessary depending on a number of factors including the desired method of administration. Such physical forms include a solid, liquid, sol, gel, aerosol, or any other physical form now known or yet to be disclosed. The concept of a pharmaceutical composition including bacteria also encompasses the bacteria without any other additive. The physical form of the composition may affect the route of administration and one skilled in the art would know to choose a route of administration that takes into consideration both the physical form of the bacteria and the desired result (e.g., colonization of the anterior nares and/or nasal cavity). Pharmaceutical compositions that include the bacteria may be prepared using methodology well known in the pharmaceutical art. A pharmaceutical composition that includes the bacteria may include a second effective compound, such as an antibiotic compound.

Pharmaceutical compositions including the bacteria may be prepared as an aerosol. Aerosols encompass a variety of systems including colloids and pressurized packages. Delivery of a composition in this form may include propulsion of a pharmaceutical composition through use of liquefied gas or other compressed gas or by a suitable pump system. Aerosols may be delivered in single phase, bi-phasic, or tri-phasic systems. Pharmaceutical compositions may be prepared for delivery on an absorbent material. In some embodiments, the composition may be delivered in the nasal cavity. In some embodiments, the composition may be delivered topically within the nasal cavity.

Pharmaceutical compositions that include the bacteria may also include a pharmaceutically acceptable carrier. Carriers include any substance that may be administered with the at least one probiotic organism with the intended purpose of facilitating, assisting, or helping the administration or other delivery of the active pharmaceutical agent. Carriers include any liquid, solid, semisolid, gel, aerosol or anything else that may be combined with the active pharmaceutical agent to aid in its administration. Examples include diluents, adjuvants, excipients, water, oils (including petroleum, animal, vegetable or synthetic oils.) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents. In some embodiments of the invention, the pharmaceutically acceptable carrier can comprise a growth medium that can support the growth and/or static existence of the bacteria in the context of the pharmaceutical composition prior to administration of the pharmaceutical composition to the subject. For example, the pharmaceutical composition can comprise one or pharmaceutically acceptable carrier to provide sufficient sustenance for the bacteria that are also compatible with the desired route of administration (e.g., intranasal administration).

The pharmaceutical composition including the active pharmaceutical agent may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

In embodiments, a composition provided herein may be administered orally or nasally and include live microorganisms (e.g., comprising, consisting essentially of, or consisting of bacteria) from $10^3$ to $10^{14}$ colony forming units (cfu)/g. In embodiments, the composition includes $10^4$ to $10^{14}$ cfu/g. In embodiments, the composition includes $10^5$ to $10^{14}$ cfu/g. In embodiments, the composition includes $10^6$ to $10^{14}$ cfu/g. In embodiments, the composition includes $10^7$ to $10^{14}$ cfu/g. In embodiments, the composition includes $10^8$ to $10^{14}$ cfu/g. In embodiments, the composition includes $10^9$ to $10^{14}$ cfu/g. In embodiments, the composition includes $10^{10}$ to $10^{14}$ cfu/g. In embodiments, the composition includes $10^{11}$ to $10^{14}$ cfu/g. In embodiments, the composition includes $10^{12}$ to $10^{14}$ cfu/g. In embodiments, the composition includes $10^{13}$ to $10^{14}$ cfu/g. In embodiments, the composition includes from $10^3$ to $10^{14}$ cfu. In embodiments, the composition includes $10^4$ to $10^{14}$ cfu. In embodiments, the composition includes $10^5$ to $10^{14}$ cfu. In embodiments, the composition includes $10^6$ to $10^{14}$ cfu. In embodiments, the composition includes $10^7$ to $10^{14}$ cfu. In embodiments, the composition includes $10^8$ to $10^{14}$ cfu. In embodiments, the composition includes $10^9$ to $10^{14}$ cfu. In embodiments, the composition includes $10^{10}$ to $10^{14}$ cfu. In embodiments, the composition includes $10^{11}$ to $10^{14}$ cfu. In embodiments, the composition includes $10^{12}$ to $10^{14}$ cfu. In embodiments, the composition includes $10^{13}$ to $10^{14}$ cfu.

EXAMPLES

Example 1: Chronic Rhinosinusitis

As detailed in the methods described below, a consecutive series of patients with CRS and healthy control subjects were recruited from January 2015 to July 2016. This study was approved by the Institutional Review Board of Rush University, and all participants provided written informed consent. Samples were collected by means of slow application of a sterile small nasal cotton swab to the middle meatus region under endoscopic guidance. Total DNA was extracted from nasal cotton swabs and processed by using high-throughput Illumina amplicon sequencing of the V4 variable region of the microbial 16S rRNA gene. Data were then clustered into OTUs at 97% similarity. Differences in the RA of individual taxa in a tiered fashion from the taxonomic levels of phylum to species were determined for significance by using Kruskal-Wallis nonparametric ANOVA corrected for false discovery rate (FDR) and accepted at a FDR P value of less than 0.05. Additionally, a subgroup analysis was conducted among patients with CRS to find potential factors that are linked to variations in the CRS microbiome.

The nasal microbiome was analyzed in association with 3 main groups of factors, including (1) demographics, (2) allergic comorbidities, and (3) CRS-related factors, including nasal polyps, number of past functional endoscopic sinus surgeries (FESSs), duration of CRS, and severity scores (Sinonasal Outcome Test [SNOT-22] score and Lund-Mackay score [LMS]).

Both conventional statistical bioinformatics analyses and an in silico approach called Phylogenetic Investigation of Communities by Reconstruction of Unobserved States (PICRUSt) were applied to infer microbiota functional pathways.[3] PICRUSt allows identification and measurement of the RA of each sample's metagenome and potential involvement in different metabolic and functional pathways needed for invasion and metabolism of bacteria, including epithelial invasion, antibacterial resistance properties, and LPS production.

One hundred eleven patients with CRS and 21 control subjects were enrolled and completed the study. The information, including patients' demographics; prevalence of allergic rhinitis, asthma, eczema, and food allergy; and CRS-related factors, including history of nasal polyps, number of FESSs, duration of CRS, SNOT-22 scores, and LMSs are detailed in Table 3 below.

The nasal microbiome analysis indicated that there were no significant differences in α-diversity between patients with CRS and control subjects. However, at the phylum level, patients with CRS had significantly lower Actinobacteria levels, which translated to lower *Corynebacterium* species levels compared with those in control subjects. Additionally, the RA of the genus *Peptoniphilus* was significantly lower in patients with CRS (Table 1). Among demographic factors, age was associated with significant bacterial RA changes. Patients with CRS younger than 30 years had significantly increased *Pseudomonas* species levels compared with patients with CRS aged between 31 and 60 years and greater than 60 years of age (Table 1).

TABLE 1

RA of selected sequences derived from individual taxa in the sinus cavities of 111 patients with CRS and 21 control subjects

| | | | | Sex | | | Age | | |
| --- | --- | --- | --- | --- | --- | --- | --- | --- | --- |
| Taxonomic level | FDR P value | RA mean in patients with CRS (n = 111) | RA mean in control subjects (n = 21) | FDR P value | RA mean in male subjects (n = 58) | RA mean in female subjects (n = 53) | FDR P value | RA mean in <30 y (n = 21) | RA mean in 31-60 y (n = 25) | RA mean in >61 y (n = 64) |
| Phyla | | | | | | | | | | |
| Actinobacteria | .006* | 1884.06 | 3548.19 | .14 | 1432.79 | 2377.91 | .14 | 1624.19 | 1546.36 | 2130.23 |
| Bacteroidetes | .895 | 194.32 | 161.90 | .46 | 167.72 | 223.42 | .46 | 294.05 | 202.24 | 153.52 |
| Firmicates | .863 | 3630.49 | 3548.43 | .82 | 3575.71 | 3690.43 | .82 | 3246.71 | 3331.64 | 3864.73 |
| Proteobacteria | .281 | 2223.83 | 1126.86 | .29 | 2459.52 | 1965.91 | .29 | 2846.43 | 2088.08 | 2061.19 |
| General | | | | | | | | | | |
| Corynebacterium | .012* | 1766.97 | 3471.86 | .08 | 1275.67 | 2304.62 | .33 | 1560.00 | 2045.73 | 1296.96 |
| Prevotella | .870 | 53.95 | 63.62 | .19 | 34.67 | 75.06 | .94 | 69.43 | 54.25 | 42.32 |
| Staphylococcus | .593 | 2174.83 | 1403.24 | .69 | 2085.22 | 2272.89 | .28 | 1360.52 | 2453.70 | 2067.24 |
| Alloiococcus | .194 | 123.56 | 587.19 | .23 | 63.33 | 189.47 | .89 | 91.76 | 158.98 | 64.52 |
| Lactobacillus | .780 | 5.50 | 1.24 | .19 | 8.36 | 2.36 | .36 | 14.00 | 3.64 | 3.28 |
| Streptococcus | .560 | 616.49 | 77.33 | .16 | 822.40 | 391.15 | .87 | 829.48 | 530.63 | 681.92 |

TABLE 1-continued

| | | | | | | | | | | |
|---|---|---|---|---|---|---|---|---|---|---|
| *Ruminococcus* | .780 | 21.10 | 10.10 | .25 | 13.55 | 29.36 | .91 | 12.67 | 21.67 | 27.48 |
| *Anaerococcus* | .478 | 219.45 | 461.90 | .47 | 191.05 | 250.53 | .26 | 328.14 | 238.89 | 87.08 |
| *Finegoldia* | .104 | 94.16 | 281.71 | .96 | 93.03 | 95.40 | .13 | 203.19 | 67.56 | 74.32 |
| *Peptoniphilus* | .007* | 144.41 | 490.90 | .54 | 162.26 | 124.89 | .42 | 223.05 | 149.98 | 69.80 |
| *Burkholderia* | .880 | 308.02 | 282.90 | .15 | 392.43 | 215.64 | .75 | 366.57 | 312.06 | 256.84 |
| *Enterobacteriaceae species* | .890 | 370.20 | 187.81 | .85 | 393.38 | 344.83 | .72 | 86.57 | 460.42 | 392.20 |
| *Haemophilus* | .881 | 198.51 | 41.10 | .23 | 85.07 | 322.66 | .85 | 179.24 | 145.59 | 358.08 |
| *Moraxella* | .890 | 156.12 | 32.33 | .43 | 219.55 | 86.70 | .46 | 1.05 | 117.33 | 391.92 |
| *Pseudomanas* | .672 | 507.42 | 44.14 | .97 | 512.76 | 501.58 | .02* | 1565.62 | 339.27 | 69.20 |

| | | Race/ethnic groups | | |
|---|---|---|---|---|
| Taxonomic level | FDR P value | RA mean in white subjects (n = 75) | RA mean in African American subjects (n = 22) | RA mean in Hispanic subjects (n = 11) |
| Phyla | | | | |
| Actinobacteria | .52 | 1710.64 | 2314.27 | 2065.09 |
| Bacteroidetes | .99 | 195.23 | 208.73 | 193.55 |
| Firmicates | .91 | 3742.24 | 3433.41 | 3068.09 |
| Proteobacteria | .94 | 2311.97 | 2168.64 | 1988.36 |
| General | | | | |
| *Corynebacterium* | .45 | 1574.17 | 2242.68 | 1969.55 |
| *Prevotella* | .99 | 55.28 | 51.86 | 63.00 |
| *Staphylococcus* | .88 | 2211.03 | 2150.23 | 1990.09 |
| *Alloiococcus* | .00 | 90.61 | 93.36 | 13.36 |
| *Lactobacillus* | .56 | 3.21 | 13.27 | 6.18 |
| *Streptococcus* | .83 | 724.63 | 265.23 | 638.55 |
| *Ruminococcus* | .68 | 17.41 | 41.18 | 11.09 |
| *Anaerococcus* | .74 | 212.48 | 306.82 | 101.91 |
| *Finegoldia* | .40 | 124.47 | 47.77 | 5.36 |
| *Peptoniphilus* | .96 | 145.92 | 158.09 | 145.91 |
| *Burkholderia* | .56 | 281.23 | 362.41 | 438.82 |
| *Enterobacteriaceae species* | .67 | 259.96 | 580.36 | 553.91 |
| *Haemophilus* | .80 | 286.49 | 9.73 | 28.91 |
| *Moraxella* | .81 | 229.11 | 3.18 | 4.91 |
| *Pseudomanas* | .96 | 537.40 | 622.73 | 209.36 |

The nasal microbiome was analyzed in patients with CRS compared with control subjects and in subgroups of patients with CRS in relation to demographic factors, including sex, age, and race/ethnicity.
*FDR P value of less than .05

TABLE 2

RA of selected sequences derived from individual taxa in the sinus cavities of 111 patients with CRS in relation to allergic rhinitis, eczema, asthma, and nasal polyps

| | | | | AR | | | Eczema | | | Polyps | |
|---|---|---|---|---|---|---|---|---|---|---|---|
| Taxonomic level | FDR P value | Asthmatic patients (n = 46) | Non asthmatic subjects (n = 65) | FDR P value | Patients with AR (n = 45) | Subjects without AR (n = 51) | FDR P value | Patient with eczema (n = 12) | Subjects without eczema (n = 99) | FDR P value | Patients with CRSwNP (n = 39) | Patients with CRSsNP (n = 72) |
| Phyla | | | | | | | | | | | | |
| Actinobacteria | .22 | 1602.59 | 2083.26 | .01* | 1179.51 | 2450.90 | .19 | 1146.67 | 1973.44 | .90 | 1902.14 | 1850.69 |
| Bacteroidetes | .93 | 190.50 | 197.02 | .43 | 137.98 | 210.00 | .39 | 101.50 | 205.57 | .48 | 213.85 | 158.26 |
| Firmicates | .59 | 3467.02 | 3746.17 | .20 | 3789.33 | 3167.61 | .01 | 5497.42 | 3404.19 | .57 | 3526.38 | 3822.69 |
| Proteobacteria | .81 | 2291.85 | 2175.69 | .57 | 2401.20 | 2308.08 | .42 | 1678.08 | 2289.98 | .65 | 2145.35 | 2368.72 |
| General | | | | | | | | | | | | |
| *Corynebacterium* | .29 | 1521.13 | 1940.95 | .01* | 1089.82 | 2298.43 | .24 | 1100.58 | 1847.75 | .72 | 1818.00 | 1672.77 |
| *Prevotella* | .22 | 31.83 | 69.62 | .33 | 32.29 | 55.25 | .29 | 7.00 | 59.65 | .72 | 57.97 | 46.54 |
| *Staphylococcus* | .20 | 1819.52 | 2426.28 | .69 | 2366.00 | 1885.33 | .08 | 3343.50 | 2033.17 | .12 | 1911.29 | 2661.36 |
| *Alloiococcus* | .34 | 63.87 | 165.80 | .37 | 40.09 | 225.61 | .42 | 1.67 | 138.33 | .70 | 138.42 | 96.13 |
| *Lactobacillus* | .41 | 3.24 | 7.09 | .69 | 3.29 | 8.49 | .75 | 3.42 | 5.75 | .48 | 6.69 | 3.28 |
| *Streptococcus* | .02* | 1037.24 | 318.72 | .09 | 753.98 | 310.80 | .01* | 1770.08 | 476.66 | .35 | 722.26 | 421.21 |
| *Ruminococcus* | .14 | 32.93 | 12.72 | .05 | 14.18 | 13.86 | .83 | 17.00 | 21.60 | .39 | 25.43 | 13.10 |
| *Anaerococcus* | .09 | 138.89 | 276.46 | .98 | 223.78 | 212.96 | .27 | 89.83 | 235.16 | .65 | 233.29 | 193.90 |
| *Finegoldia* | .22 | 61.20 | 117.49 | .71 | 101.87 | 107.10 | .33 | 31.50 | 101.76 | .46 | 81.82 | 116.95 |
| *Peptoniphilus* | .23 | 101.17 | 175.02 | .87 | 170.04 | 135.37 | .48 | 81.83 | 152.00 | .40 | 125.42 | 179.49 |
| *Burkholderia* | .05 | 383.04 | 254.92 | .16 | 396.29 | 273.61 | .85 | 327.75 | 305.63 | .24 | 339.81 | 249.33 |
| *Enterobacteriaceae* | .80 | 331.72 | 397.43 | .70 | 221.56 | 428.35 | .33 | 17.33 | 412.97 | .75 | 399.07 | 316.90 |

TABLE 2-continued

RA of selected sequences derived from individual taxa in the sinus cavities of
111 patients with CRS in relation to allergic rhinitis, eczema, asthma, and nasal polyps

|  |  |  |  | AR | | | Eczema | | | Polyps | |
| --- | --- | --- | --- | --- | --- | --- | --- | --- | --- | --- | --- |
| Taxonomic level | FDR P value | Asthmatic patients (n = 46) | Non asthmatic subjects (n = 65) | FDR P value | Patients with AR (n = 45) | Subjects without AR (n = 51) | FDR P value | Patient with eczema (n = 12) | Subjects without eczema (n = 99) | FDR P value | Patients with CRSwNP (n = 39) | Patients with CRSsNP (n = 72) |
| *Haemophilus* | .41 | 102.24 | 266.65 | .94 | 271.58 | 161.22 | .54 | 23.08 | 219.78 | .13 | 89.94 | 398.95 |
| *Moraxella* | .71 | 119.30 | 182.17 | .99 | 123.09 | 180.24 | .52 | 2.42 | 174.75 | .79 | 139.46 | 186.87 |
| *Pseudomanas* | .49 | 649.96 | 406.55 | .74 | 528.18 | 629.22 | .57 | 787.42 | 473.48 | .46 | 412.44 | 682.77 |

AR, Allergic rhinitis;
CRSsNP, chronic rhinosinusitis without nasal polyps;
CRSwNP, chronic sinusitis with nasal polyps.
*FDR P value less than .05.

PICRUSt analysis showed that LPS biosynthesis proteins and bacterial invasion of epithelial cell pathways were significantly greater in patients with CRS. Additionally, allergic rhinitis was associated with an increased abundance of the LPS biosynthesis protein pathway (Table 5).

To date, this is the largest study analyzing the nasal microbiome in patients with CRS. The large number of patients with CRS enabled us to test the association of multiple CRS-related variables with the nasal microbiome. Furthermore, we used meticulous methods in subject recruitment, sample collection, and specimen handling to avoid the common biases seen in some previous studies. Our study of 111 patients with CRS and one previous study with more than 50 patients with CRS[4] have shown that the bacterial diversity and richness of the nasal cavity does not significantly change in patients with CRS.

Genera that were decreased significantly in patients with CRS compared with control subjects were *Corynebacterium* and *Peptoniphilus*. Our findings are in agreement with previous studies reporting a significant decrease in *Peptoniphilus* species in patients with CRS[4] and *Corynebacterium* species in patients with CRS without nasal polyps.[5] *Peptoniphilus* is an anaerobic genus of bacteria from the Clostridia class that has been found in the nasal cavity from the first studies that evaluated the nasal microbiome by using non-culture-based methods.[6] Clostridia-containing microbiota have been shown to downregulate innate lymphoid cell function and hence to decrease the allergic response and subsequent $T_H2$ inflammation, effects that might diminish the likelihood of development of a type 2 disease.[7] Decreased colonization with certain bacteria from the Clostridia family might remove a protective element and promote $T_H2$ inflammation and progression of upper respiratory tract inflammation, potentially contributing to the pathogenesis, progression, or both of patients with CRS, especially in those with atopy.

We found that among patients with CRS, those with allergic rhinitis had lower RA of *Corynebacterium* species compared with nonallergic patients with CR. More notably, patients with CRS without allergic rhinitis had similar levels of this organism compared with control subjects, suggesting that the diminution of Corynebacteriumspecies might more reflect the type 2 milieu than CRS disease. In a previous study increased abundance of *Corynebacterium* species at the time of endoscopic sinus surgery was predictive of better surgical outcomes.[4] This indicates a potential protective role for *Corynebacterium* species in maintaining the health of the sinus mucosa. It is noteworthy that the genus *Corynebacterium* in the nasal cavity is believed to be important for maintaining a sustained and stable microbial pattern in healthy infants.[8]

In our study atopic dermatitis was associated with a higher RA of *Streptococcus* species. Colonization of the skin with a microbiome enriched for *Streptococcus* species is seen in atopic dermatitis-prone skin[9] and associated with disease severity. This higher RA of *Streptococcus* species in patients with atopic CRS along with further decreased RA of *Corynebacterium* species in patients with allergic rhinitis suggests that the imbalance between these 2 bacterial genera might be an important factor in defying a certain atopic endotype in patients with CRS.

PICRUSt analyses inferred that the resident bacterial community modifies its functional patterns in patients with CRS, and bacteria with the ability to invade the epithelium and increase production of LPS have overcome the microbial community in patients with CRS. The lack of increase of abundance of any single known LPS-producing bacterium suggests that there might be different cohorts of diverse LPS producers that are increased in individual patients with CRS. This suggests that future efforts should target discovery of the bacterial groups with functional capacities that enable them to overcome the community in disease or in a certain phenotype of disease, which could provide us with clues of how bacteria are contributing or even initiating a disease process.

The results above showing a link between specific genera and CRS-related factors suggest that the nasal microbiome could be used as a tool to characterize and identify endotypes of patients with CRS.

Methods

Patients

A consecutive series of patients with CRS who underwent evaluation in the Department of Otorhinolaryngology-Head and Neck Surgery at Rush University Medical Center were recruited from January 2015 to July 2016. Patients with CRS who received oral or topical antibiotics or oral steroids in the 3 months before enrollment were excluded. The CRS diagnosis was based on 12 weeks of persistent sinonasal symptoms, with objective findings based on endoscopy, computed tomographic sinus imaging, or both. A group of healthy control subjects without a history of sinus or allergic disease were also enrolled. All patients were evaluated clinically by an allergist to confirm or properly rule out asthma and allergic conditions. This study was approved by the Institutional Review Board of Rush University Medical Center, and all participants provided written informed consent. Samples were collected by means of slow application of a sterile small nasal cotton swab to the middle meatus region under endoscopic guidance. The cotton swab heads were placed in sterile tubes and frozen at −80° C. within 1 hour of sampling until the time of DNA extraction.

Microbiome Analyses

Total DNA was extracted from nasal cotton swabs by using a commercially available kit (Fast DNA Spin Kit; MP Biomedicals, Solon, Ohio), according to the manufacturer's recommended protocol. DNA was processed by using high-throughput Illumina amplicon sequencing of the V4 variable region of the microbial 16S rRNA gene[10] and implementing a modified 2-step targeted amplicon sequencing approach.[11] Negative controls were used with each set of amplification, which indicated no contamination. Raw sequence data (FASTQ files) were deposited in the National Center for Biotechnology Information Sequence Read Archive under project PRJNA395923. Raw FASTQ files for each sample were processed to merge reads, remove low-quality data and chimeras, and perform annotation with the Greengenes 13_8 reference database, as previously described.[12,13] Data were then clustered into OTUs at 97% similarity, and the sample sequence set was rarefied to 4400 sequences.[13] α-Diversity indices were calculated by using the software package Primer7.[14] We applied both conventional statistical bioinformatics analyses to interrogate microbiota composition in nasal cavity and also used an in silico approach called PICRUSt to infer microbiota functional pathways.[15] During the process of DNA amplification in nasal microbiome analysis, a significant number of short DNA fragments are generated. PICRUSt allows identification and measurement of the RA of each sample's metagenome and potential involvement in different metabolic and functional pathways needed for invasion and metabolism of bacteria, including epithelial invasion, antibacterial resistance properties, and production of LPS.

Biostatistics

Microbial community analysis was done in a tiered fashion from the taxonomic levels of phylum to species. Differences in the RA of individual taxa (>1% of data set) were determined for significance by using Kruskal-Wallis nonparametric ANOVA. The RA of individual taxa reported was corrected for FDR and accepted at an FDR Pvalue of less than 0.05. Bioinformatics analyses were used to test differences in nasal microbiota composition and identify key taxa that were most strongly altered when comparing CRS with control samples.

In addition, a subgroup analysis was conducted among patients with CRS to find potential factors linked to variations in the CRS microbiome. The 5 most abundant phyla and 15 most abundant genera were chosen for the subgroup analysis. Associations between the RA of each OTU and nominal and continuous variables were assessed by using ANOVA and Spearman correlation tests, as appropriate. For statistical analyses, SPSS software (version 21.0; SPSS, Chicago, Ill) was used. Significance was accepted at a P value of less than 0.05 corrected for multiple analyses. Graphs were created by using GraphPad Prism (version 5.00; GraphPad Software, La Jolla, Calif) software.

TABLE 3

Demographic and clinical characteristics of 111 patients with CRS and 21 control subjects

| Characteristic | Patients with CRS | Control subjects | P value, $X^2$ or t test |
|---|---|---|---|
| Sex | | | |
| Male | 58 | 13 | .28 |
| Female | 53 | 8 | |
| Age (y), mean ± SD | 47.34 ± 15.47 | 52 ± 13.7 | .31 |
| BMI (kg/m$^2$), mean ± SD | 29.42 ± 6.22 | 31.30 ± 7.23 | .21 |
| Nasal polyps | | | |
| CRSsNP | 39 | NA | — |
| CRSwNP | 72 | | |
| Asthma | | | |
| Yes | 46 | 3 | .006 |
| No | 65 | 17 | |
| Not known | 0 | 1 | |
| AERD | | | |
| Yes | 18 | NA | — |
| No | 93 | | |
| Atopy | | | |
| Negative skin test result | 52 | 15 | .015 |
| Positive skin test result | 45 | 1 | |
| No skin test* | 14 | 5 | |
| Eczema | | | |
| Yes | 12 | 1 | .004 |
| No | 99 | 20 | |
| Food allergy | | | |
| Yes | 12 | 2 | .093 |
| No | 99 | 19 | |
| LMS, mean ± SD | 9.46 ± 7.07 | NA | — |
| No. of surgeries, mean ± SD† | 1.81 ± 1.82 | NA | — |
| Duration of CRS (y), mean ± SD | 12.43 ± 10.28 | NA | — |
| Total SNOT-22 scores | 32.57 ± 24.65 | 13.28 ± 20.9 | .001 |

AERD, Aspirin-exacerbated respiratory disease;
CRSsNP, Chronic rhinosinusitis without nasal polyps;
CRSwNP, chronic sinusitis with nasal polyps;
NA, not applicable.
*This case with unknown asthma status had breathing symptoms but normal office spirometric results and was lost to follow-up for further advanced testing for asthma.
†Range for number of previous sinus surgeries was 0 to 8.

TABLE 4

Correlation between RA of selected sequences derived from individual taxa and CRS symptom scores measured by using SNOT-22 scores and LMSs in 111 patients with CRS

| | SNOT-22 score | | LMS | |
|---|---|---|---|---|
| Taxonomic level | Correlation coefficient (R) | FDR P value | Correlation coefficient (R) | FDR P value |
| Phyla | | | | |
| Actinobacteria | −0.043 | .651 | −0.054 | .576 |
| Bacteroidetes | −0.015 | .874 | −0.002 | .984 |
| Firmicutes | 0.041 | .670 | −0.070 | .465 |
| Proteobacteria | 0.052 | .586 | 0.138 | .150 |
| Genera | | | | |
| Corynebacterium | −0.050 | .600 | −0.053 | .578 |
| Prevotella | −0.233 | .014* | 0.064 | .507 |
| Staphylococcus | 0.039 | .684 | −0.117 | .220 |
| Alloiococcus | 0.040 | .675 | 0.019 | .840 |
| Lactobacillus | −0.114 | .233 | 0.097 | .312 |
| Streptococcus | 0.111 | .246 | 0.036 | .709 |
| Ruminococcus | 0.040 | .679 | −0.055 | .566 |
| Anaerococcus | −0.158 | .097 | −0.032 | .740 |

TABLE 4-continued

Correlation between RA of selected sequences derived from individual taxa and CRS symptom scores measured by using SNOT-22 scores and LMSs in 111 patients with CRS

| Taxonomic level | SNOT-22 score | | LMS | |
|---|---|---|---|---|
| | Correlation coefficient (R) | FDR P value | Correlation coefficient (R) | FDR P value |
| Finegoldia | −0.100 | .297 | −0.119 | .213 |
| Peptoniphilus | −0.131 | .171 | −0.080 | .405 |
| Burkholderia | 0.070 | .463 | −0.095 | .322 |
| Enterobacteriaceae | −0.043 | .657 | 0.189 | .045* |
| Haemophilus | −0.004 | .963 | 0.065 | .496 |
| Moraxella | 0.029 | .760 | 0.092 | .337 |
| Pseudomonas | −0.112 | .243 | −0.164 | .086 |

The correlation of higher SNOT-22 scores with low RA of *Prevotella* species is in agreement with studies in lower airways showing that *Prevotella* species are decreased in airways of patients with asthma and chronic obstructive pulmonary diseaseE7 and negatively correlated with markers of inflammation. E8A higher LMS was correlated with increased Enterobacteriaceae species levels, which is in agreement with studies showing a correlation between this genus and airway inflammation in patients with other chronic inflammatory diseases, such as cystic fibrosis. * P<0.05.

TABLE 5

Differences in selected KEGG pathways using PICRUSt analysis of nasal microbiomes

| | Patients with CRS vs control subjects | | | | Patients with CRS with allergic rhinitis vs patients with CRS without allergic rhinitis | | | |
|---|---|---|---|---|---|---|---|---|
| Pathway | Patients with CRS, RA mean | Control subjects, RA mean | Patients with CRS/control subjects, ratio | P value* | Patients with CRS with AR, RA mean | Patients with CRS without AR, RA mean | Patients with CRS with AR/CRS without AR, ratio | P value* |
| Bacterial invasion of epithelial cella | 191,003.76 | 63,446.76 | 3.01 | .03* | 228,467.99 | 154,631.88 | 1.47 | .11 |
| LPS biosynthesis proteins | 74,341.98 | 32,890.76 | 2.26 | .04* | 98,073.42 | 34,233.58 | 2.86 | .04* |
| Bacterial toxin production | 49,787.94 | 21,994.04 | 2.26 | .09 | 42,846.76 | 53,209.27 | 1.24 | .67 |
| RNA transport | 20,471.63 | 11,123.90 | 1.84 | .26 | 23,423.63 | 17,433.20 | 1.34 | .24 |
| β-Lactam resistance | 9,167.56 | 5,300.62 | 1.72 | .23 | 10,178.52 | 8,350.42 | 0.82 | .86 |
| Bacterial motility | 152,008.65 | 108,989.38 | 1.39 | .40 | 142,468.64 | 154,781.02 | 1.08 | .87 |
| Bacterial chemotaxis | 234.18 | 174.80 | 1.33 | .54 | 150.31 | 165.18 | 1.09 | .79 |
| Bacterial secretion system | 17,863.96 | 15,339.47 | 1.16 | .87 | 17,346.11 | 17,887.11 | 1.03 | .91 |

AR, Allergic rhinitis.
*Kruskal-Wallis nonparametric 1-way ANOVA: P <.05.

Example 2 Asthma

Asthma is a related chronic inflammatory disease of the lower airways that is often comorbid with CRS. Uncontrolled upper airway inflammation in the context of CRS is associated with lower airway T-helper-2-mediated inflammation and recalcitrant asthma, however; the underlying mechanism of this link is rather complicated and currently under investigation.[18] Rhinosinusitis is also linked to increased asthma severity and exacerbation rate.[19] Nevertheless, fundamental questions regarding the mechanisms of chronic mucosal inflammation in CRS and how chronic sinonasal inflammation may affect the lower airways remain unanswered. Considering the likely possibility that microorganisms extant in the upper airways will be aspirated into the lungs, studies of the sinonasal microbiome in the context of lung health appear to be worthwhile. Microbiome studies provide important knowledge about both commensal and pathogenic microbes residing in the airways.[2] Prior studies have shown that CRS patients have significant differences in nasal micro biomes compared to healthy individuals,[2] and one study reported further differentiation between CRS patients with or without asthma.[20] In the present study, we investigated whether the composition of the nasal microbiome is associated with asthma control and severity in patients with comorbid CRS.

The cohort of 111 CRS patients visiting a tertiary care centre discussed above in Example 1 were included in this prospective study.[21] Diagnosis of CRS was confirmed with at least 12 weeks of rhinosinusitis symptoms and evidence of sinusitis in computer tomography scans based on European position paper on rhinosinusitis (EPOS) 2012 criteria.[22] Exclusion criteria included use of antibiotics within 3 months or undergoing FESS 6 months prior to sampling. Samples for microbiome analysis were collected by rhinologists experienced in nasal sample collection after complete nasal endoscopy, using endoscopy guided small size nasal swabs from the middle meatus. All cases underwent thorough assessment for allergic conditions and asthma by an allergist. Individuals with asthma, confirmed per GINA (Global Initiative for Asthma) criteria, completed an Asthma Control Test (ACT) on the day of nasal swabbing and underwent an office spirometry (performed within 2 months of sample collection). Enrolled asthmatics were interviewed using a questionnaire that captures information about current asthma control, asthma emergency room (ER) visits and hospitalization during the two-year period prior to the study.

Additionally, all participating patients were followed up for 12 months for asthma-related events, including ER visits or hospitalizations. Asthmatic CRS patients were grouped based on ACT scores (ACT≥20, ACT<20) and FEV1 performance which was done in our office (Group 1: FEV1≤60% predicted, Group 2: FEV1 61-75% predicted, Group 3: FEV1≥76% predicted). Furthermore, patients were divided using the National Institutes of Health Expert Panel Report 3 (EPR-3) asthma guidelines into intermittent, mild, moderate and severe persistent asthmatic groups. Mild and moderate persistent asthmatics were merged due to their small numbers (7 mild, 9 moderate). Microbiome composition was analysed using 16S ribosomal RNA sequencing of the V4 region as described previously,[21] and data were clustered into operational taxonomic units (OTUs) at 97% similarity. Alpha-diversity indices were calculated within the software package Primer7. The relative abundance of individual taxa from the taxonomic levels of phylum to genus was compared independently from alpha indices results and reported using the Kruskal-Wallis nonparametric analysis of variance tests, corrected for false discovery rate and accepted at a significance of (FDR-P<0.05). This study was approved by Rush University Institutional review board and all participants signed consent forms.

Among 111 CRS cases, 46 (41.4%) had concurrent physician-diagnosed asthma per GINA criteria which included clinical investigations and spirometry measurements. Of note, there was no difference between asthmatics and nonasthmatics in terms of demographic factors, nasal polyps, number of past functional endoscopic sinus surgeries, duration of CRS, sinonasal outcome test score (SNOT-22) and Lund Mackay score (LMS). Asthmatic patients had higher rates of allergic rhinitis (AR) diagnosed based on rhinitis symptoms plus positive skin prick test results to aeroallergens (60.9% asthmatic vs. 26.2% nonasthmatic, P<0.05).

There were no significant differences in alpha-diversity between CRS patients with and without asthma. However, compared to nonasthmatic CRS patients, asthmatic CRS had significantly higher relative abundance (RA) of the *Streptococcus* genus, with a mean of 1037.2 vs. 318.7, P=0.001. Asthmatic CRS also trended towards increased *Burkholderia* genera abundance, with a mean of 685.8 vs. 285.8, P=0.083. Overall, 8 (17%) asthmatics had at least one ER visit due to asthma exacerbation in the three-year period (two years prior and one-year follow-up). Asthma-related ER visits were associated with significant nasal microbiome changes. RA of Proteobacteria phylum was significantly higher in asthmatics with ER visits vs. asthmatics without ER visits (mean±SD of 4287.1±3047.4 vs. 1835.1±2170.8, P=0.02). Furthermore, *Burkholderia* within this phylum was significantly increased in asthmatics with at least one ER visit (mean±SO of 685.8±894.4 vs. 319.3±324.2, P=0.02). Patients in Group 1 (FEV1≤60%) trended towards increased *Burkholderia* compared to Groups 2 and 3 (those with FEV1 61-75% and FEV1 ≥76%, respectively); with mean±SO of 705.35±701.38, 411.62±402.05 and 234.6±262.5 in Groups 1, 2 and 3, respectively, P=0.067. No significant variation existed in nasal microbiomes associated with NIH EPR-3 categories or ACT scores. There were no significant differences in terms of alpha-diversity indices of nasal bacterial communities associated with asthma ER visits, FEV1 groups or ACT groups. All results remained unchanged after adjusting for age, gender and allergic rhinitis by logistic regression analysis.

We have recently shown that CRS is associated with changes in the nasal microbiome.[21] The findings of this current prospective study provide additional evidence that nasal microbial populations vary between patients with both asthma and CRS and those with just CRS alone regardless of the presence of AR. It is tempting to speculate that alterations in upper airway microbial flora in CRS may facilitate the onset or severity of asthma in the lower airways. In agreement with one prior study,[20] we found CRS patients with asthma have significantly different nasal microbiota compared to those without asthma. Specifically, the RA of *Streptococcus* was elevated in asthmatic CRS versus nonasthmatic CRS. *Streptococcus* is one of the most frequently captured genera in both culture-based and sequencing CRS studies.[2] Importantly, early asymptomatic colonization of upper airways with *Streptococcus* in infancy is linked to early childhood wheezing[23] and strongly predicts asthma.[23,24] Our results reinforce the link between this genus and asthma in adult CRS patients, directing future studies to evaluate the underlying mechanism of this observed association.

The increase in Proteobacteria in asthmatics with ER visits during the study reflects prior findings in lower respiratory tracts of asthmatics, in which genera within this phylum are found to be elevated.[25] The asthmatic group also had increasing trend of *Burkholderia*, a genus within Proteobacteria. Further, the same trend was magnified in the asthmatic CRS group with ER visits and trended towards significance in association with low FEV1. Interestingly, colonization with the species *Burkholderia* Cepada is associated with decreased FEV1 in patients with cystic fibrosis (CF).[26] Other *Burkholderia* species are notorious for their virulence and can result in significant inflammatory response in lower airways.[27] Sinuses have been shown to act as a reservoir for these organisms, potentially linked to lower airways infection and inflammation.[28] Our data may point out to a link between upper airways colonization of these bacteria and inflammation in lower airways, echoing observations made in bacteria that colonize both upper and lower airways of CF patients.[29] In reverse, initial colonization of lower airways may act as a reservoir and source for upper airways bacteria.

Limitations of this study include absence of healthy controls and subsequently a reference sinonasal microbiome for comparison, As the sampling was performed by passing a swab through nasal passage, despite all efforts and use of very small swabs, there is possibility of contamination of the sample by the nasal vestibular flora, In addition, we have excluded 12 cases in the data point regarding FEV1 measurement, as spirometry measurements were taken over one week apart from sampling due to logistic issues, which, however, did not affect final results. Whether microbiome changes are a cause or an effect of allergic and inflammatory diseases remains to be studied. Microbiota imbalances could be the initial trigger of immune reaction and inflammation. A dysfunctional immune barrier along with an inflamed mucosal epithelium can promote suitable conditions for certain microorganisms and dysbiosis. In addition, multiple topical and systemic medications that patients with airways diseases are often treated with may affect the local microbiome. The observed trend towards an association of increased *Burkholderia* RA with asthma severity and poor outcome (increased ER visits) in CRS indicates a possible role for this bacterium and a mechanism by which CRS may affect asthma, calling for further investigations.

Example 3 Treatment of Sinusitis

A subject with sinusitis, for example, chronic rhinosinusitis (CRS) will be administered a composition including bacteria from the genus *Corynebacterium* and/or bacteria from the genus *Peptoniphilus*. The composition will be administered to the subject's nasal cavity. One or more administrations will be delivered to the subject as determined by a medical professional. The bacteria from the genus *Corynebacterium* and/or bacteria from the genus *Peptoniphilus* will be isolated from a family member.

Example 4 Treatment of Sinusitis

A subject with sinusitis, for example, CRS will be administered a composition including bacteria from the genus *Corynebacterium* and/or bacteria from the genus *Peptoniphilus*. The composition will be administered to the subject's nasal cavity. One or more administrations will be delivered to the subject as determined by a medical professional. The bacteria from the genus *Corynebacterium* and/or bacteria from the genus *Peptoniphilus* will be obtained from a commercially available source. For example, the bacteria from the genus *Corynebacterium* and/or bacteria from the genus *Peptoniphilus* may be obtained from the American Type Culture Collection (ATCC) and Leibniz Institute DSMZ-German Institute of Microorganisms and Cell Cultures (DSMZ).

Example 5 Treatment of Sinusitis

A subject with CRS will be treated by restoring the subject's own microbiome to a normal balance. An isolate for culture in vitro will be obtained from the nasal cavity of the subject and cultured in vitro. The isolate from the subject will be tested using the microbiome analysis described in Example 1 to determine the imbalance in the microbiome. In vitro, the isolate will be cultured to return the isolate to the normal microbiome, for example, by increasing the amount of bacteria from the genus *Corynebacterium* and/or bacteria from the genus *Peptoniphilus* in the isolate. The subject's own normalized isolate will be administered to the subject.

Example 6 Treatment of Asthma

A subject with asthma and CRS will be administered a composition including bacteria from the genus *Corynebacterium* and/or bacteria from the genus *Peptoniphilus* to treat the asthma by restoring a normal balance of the subject's microbiome. In some subjects, an agent that is bacteriostatic or bactericidal to the genus *Streptoococcus* and/or the genus *Burkholderia* before, after or concurrently with the composition including bacteria from the genus *Corynebacterium* and/or bacteria from the genus *Peptoniphilus*.

Example 7 Microbiome Analysis

Microbiome analysis according to Example 1 will be performed on the subjects of Examples 3-6 before administering the composition to the subject. The microbiome analysis may also be performed after administering the composition to the subject and after one or more subsequent administrations of the composition.

Example 8 Animal Model

An animal model, for example of CRS, will be used to determine the restoration of the microbiome from the CRS microbiome to the normal microbiome of a human subject. The animal model restoration of the microbiome may be confirmed by the microbiome analysis according to Example 1.

The above FIGURES and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. Bachert, C., Zhang, N., van Zele, T., Gevaert, P., Patou, J., and van Cauwenberge, P. *Staphylococcus aureus* enterotoxins as immune stimulants in chronic rhinosinusitis. *Clin Allergy Immunol.* 2007; 20:163-175.
2. Mahdavinia, M., Keshavarzian, A., Tobin, M. C., Landay, A. L., and Schleimer, R. P. A comprehensive review of the nasal microbiome in chronic rhinosinusitis (CRS). *Clin Exp Allergy.* 2016; 46:21-41.
3. Langille, M. G., Zaneveld, J., Caporaso, J. G., McDonald, D., Knights, D., Reyes, J. A. et al. Predictive functional profiling of microbial communities using 16S rRNA marker gene sequences. *Nat Biotechnol.* 2013; 31:814-821.
4. Ramakrishnan, V. R., Hauser, L. J., Feazel, L. M., Ir, D., Robertson, C. E., and Frank, D. N. Sinus microbiota varies among chronic rhinosinusitis phenotypes and predicts surgical outcome. *J Allergy Clin Immunol.* 2015; 136:334-342.e1.
5. Lal, D., Keim, P., Delisle, J., Barker, B., Rank, M. A., Chia, N. et al. Mapping and comparing bacterial microbiota in the sinonasal cavity of healthy, allergic rhinitis, and chronic rhinosinusitis subjects. *Int Forum Allergy Rhinol.* 2017; 7:561-569.
6. Stephenson, M. F., Mfuna, L., Dowd, S. E., Wolcott, R. D., Barbeau, J., Poisson, M. et al. Molecular characterization of the polymicrobial flora in chronic rhinosinusitis. *J Otolaryngol Head Neck Surg.* 2010; 39:182-187.
7. Stefka, A. T., Feehley, T., Tripathi, P., Qiu, J., McCoy, K., Mazmanian, S. K. et al. Commensal bacteria protect against food allergen sensitization. *Proc Natl Acad Sci USA.* 2014; 111:13145-13150.
8. Biesbroek, G., Tsivtsivadze, E., Sanders, E. A., Montijn, R., Veenhoven, R. H., Keijser, B. J. et al. Early respiratory microbiota composition determines bacterial succession patterns and respiratory health in children. *Am J Respir Crit Care Med.* 2014; 190:1283-1292.
9. Chang, K. R., Tay, A. S., Li, C., Ng, A. H., Wang, J., Suri, B. K. et al. Whole metagenome profiling reveals skin microbiome-dependent susceptibility to atopic dermatitis flare. *Nat Microbiol.* 2016; 1:16106.
10. Caporaso, J. G., Lauber, C. L., Walters, W. A., Berg-Lyons, D., Huntley, J., Fierer, N. et al. Ultra-high-throughput microbial community analysis on the Illumina HiSeq and MiSeq platforms. *ISME J.* 2012; 6:1621-1624.
11. Green, S. J., Venkatramanan, R., and Naqib, A. Deconstructing the polymerase chain reaction: understanding and correcting bias associated with primer degeneracies and primer-template mismatches. *PLOS One.* 2015; 10: e0128122.

12. Keshavarzian, A., Green, S. J., Engen, P. A., Voigt, R. M., Naqib, A., Forsyth, C. B. et al. Colonic bacterial composition in Parkinson's disease. *Mov Disord.* 2015; 30:1351-1360.
13. Gihring, T. M., Green, S. J., and Schadt, C. W. Massively parallel rRNA gene sequencing exacerbates the potential for biased community diversity comparisons due to variable library sizes. *Environ Microbiol.* 2012; 14:285-290.
14. Clarke, K. R. Non-parametric multivariate analyses of changes in community structure. *Aust J Ecol.* 1993; 18:117-143.
15. Langille, M. G., Zaneveld, J., Caporaso, J. G., McDonald, D., Knights, D., Reyes, J. A. et al. Predictive functional profiling of microbial communities using 16S rRNA marker gene sequences. *Nat Biotechnol.* 2013; 31:814-821.
16. Hilty, M., Burke, C., Pedro, H., Cardenas, P., Bush, A., Bossley, C. et al. Disordered microbial communities in asthmatic airways. *PLOS One.* 2010; 5: e8578.
17. Zemanick, E. T., Wagner, B. D., Robertson, C. E., Stevens, M. J., Szefler, S. J., Accurso, F. J. et al. Assessment of airway microbiota and inflammation in cystic fibrosis using multiple sampling methods. *Ann Am Thorac Soc.* 2015; 12:221-229.
18. Lee T J, Fu C H, Wang C H, et al. Impact of chronic rhinosinusitis on severe asthma patients. *PLOS ONE.* 2017; 12 (2): e0171047.
19. Dixon A E, Kaminsky D A, Holbrook J T, Wise R A, 5hade D M, Irvin C G. Allergic rhinitis and sinusitis in asthma: differential effects on symptoms and pulmonary function. Chest. 2006; 130 (2): 429-435.
20. Ramakrishnan V R, Hauser L J, Feazel L M, Ir D, Robertson C E, Frank D N. Sinus microbiota varies among chronic rhinosinusitis phenotypes and predicts surgical outcome. J Allergy Clin Immunol. 2015; 136 (2): 334-342. e1.
21. Mahdavinia M, Engen P A, LoSavio P S, et al. The nasal microbiome in patients with chronic rhinosinusitis: Analyzing the effects of atopy and bacterial functional pathways in 111 patients. J Allergy Clin Immunol. 2018; 142:287-290.
22. Fokkens W J, Lund V J, Mullol J, et al. EPOS 2012: European position paper on rhinosinusitis and nasal polyps 2012. A summary for otorhi-nolaryngologists. Rhinology. 2012; 50 (1): 1-12.
23. Cardenas P A, Cooper P J, Cox M J, et al. Upper airways microbiota in antibiotic-naive wheezing and healthy infants from the tropics of rural Ecuador. PLoS ONE. 2012; 7 (10): e46803.
24. Teo S M, Mok D, Pham K, et al. The infant nasopharyngeal microbiome impacts severity of lower respiratory infection and risk of asthma development. Cell Host Microbe. 2015; 17 (5): 704-715.
25. Huang Y J, Marsland B J, Bunyavanich S, et al. The microbiome in allergic disease: current understanding and future opportunities-2017 PRACTALL document of the American academy of allergy, asthma & immunology and the European academy of allergy and clinical immunology. J Allergy Clin Immunol. 2017; 139 (4): 1099-1110.
26. Navarro J, Rainisio M, Harms H K, et al. Factors associated with poor pulmonary function: cross-sectional analysis of data from the ERCF. European Epidemiologic Registry of Cystic Fibrosis. Eur Respir J. 2001; 18 (2): 298-305.
27. David J, Bell R E, Clark G C. Mechanisms of disease: host-pathogen interactions between *burkholderia* species and lung epithelial cells. Front Cell Infect Microbiol. 2015; 5:80.
28. Aanaes K. Bacterial sinusitis can be a focus for initial lung colonisation and chronic lung infection in patients with cystic fibrosis. J Cyst Fibros. 2013; 12 (Suppl 2): 51-520.
29. Lucas S K, Yang R, Dunitz J M, Boyer H C, Hunter R C. 165 rRNA gene sequencing reveals site-specific signatures of the upper and lower airways of cystic fibrosis patients. J Cyst Fibros. 2018; 17 (2): 204-212.

We claim:

1. A method for treating sinusitis in a subject, the method comprising:
   administering to the subject an effective amount of a composition comprising *Peptoniphilus* bacteria, wherein the composition inhibits growth of a genus of bacteria of one or more of *Streptococcus* and *Burkholderia*.
2. The method according to claim 1, wherein the sinusitis is chronic rhinosinusitis (CRS).
3. The method according to claim 1, wherein the subject has asthma.
4. The method according to claim 1, wherein the composition further comprises *Corynebacterium*.
5. The method according to claim 3, further comprising inhibiting growth of the genus *Streptococcus*.
6. The method according to claim 3, further comprising inhibiting growth of the genus *Burkholderia*.
7. The method according to claim 3, further comprising inhibiting growth of the genus *Streptococcus* and the genus *Burkholderia*.
8. The method according to claim 1, wherein the composition comprises a bacterial composition that is harvested from a normal subject.
9. The method according to claim 8, wherein the bacterial composition is processed to isolate bacteria from the genus *Peptoniphilus*.
10. The method according to claim 1, wherein the composition is administered intranasally.
11. The method according to claim 1, wherein the composition comprises a liquid, foam, cream, spray, powder, gel, or absorbent material.
12. The method according to claim 1, wherein a microbiome of the subject is analysed before administering the composition.
13. The method according to claim 1, wherein a microbiome of the subject is analysed after the administration of the composition.

* * * * *